US010743795B2

(12) United States Patent
Morris et al.

(10) Patent No.: US 10,743,795 B2
(45) Date of Patent: Aug. 18, 2020

(54) METHOD AND APPARATUS FOR LIMB CIRCUMFERENCE MEASUREMENT

(71) Applicant: AT&T INTELLECTUAL PROPERTY I, L.P., Atlanta, GA (US)

(72) Inventors: Nadia Morris, Houston, TX (US); Mohamed Mohamed, Houston, TX (US); Shaoda Yu, Katy, TX (US)

(73) Assignee: AT&T Intellectual Property I, L.P., Atlanta, GA (US)

(*) Notice: Subject to any disclaimer, the term of this patent is extended or adjusted under 35 U.S.C. 154(b) by 306 days.

(21) Appl. No.: 15/656,527

(22) Filed: Jul. 21, 2017

(65) Prior Publication Data

US 2019/0021634 A1 Jan. 24, 2019

(51) Int. Cl.
*A61B 5/107* (2006.01)
*G01B 7/28* (2006.01)
(Continued)

(52) U.S. Cl.
CPC ............ *A61B 5/1077* (2013.01); *A41H 1/02* (2013.01); *A61B 5/0004* (2013.01); *A61B 5/1072* (2013.01); *A61B 5/6807* (2013.01); *A61B 5/7278* (2013.01); *A61B 5/742* (2013.01); *G01B 5/025* (2013.01); *G01B 7/12* (2013.01); *G01B 7/18* (2013.01); *G01B 7/28* (2013.01); *G01B 7/287* (2013.01); *A61B 2560/0475* (2013.01)

(58) Field of Classification Search
None
See application file for complete search history.

(56) References Cited

U.S. PATENT DOCUMENTS 3,812,844 A   5/1974   Sokol et al.
4,429,699 A   2/1984   Hatschek
(Continued)

FOREIGN PATENT DOCUMENTS

WO   2005067796 A1   7/2005
WO   2010093668 A1   8/2010
(Continued)

OTHER PUBLICATIONS

Feliciani, Giacomo et al., "Cold pressor test using strain-gauge plethysmography", Advances in Physiology Education 40.3, 2016, 410-417.

(Continued)

*Primary Examiner* — Douglas X Rodriguez
(74) *Attorney, Agent, or Firm* — Guntin & Gust, PLC; Matthew Bruce Tropper

(57) ABSTRACT

Aspects of the subject disclosure may include, for example, obtaining a first plurality of circumference measurements, each of the first plurality of circumference measurements corresponding to a first circumference around a limb of a person at a respective one of a plurality of locations of the limb, each of the first plurality of circumference measurements being obtained from a respective one of a plurality of elastic measurement elements that is positioned at a respective one of the locations; determining, based upon the first plurality of circumference measurements, a first geometric profile along a length of the limb; and outputting data representing the first geometric profile. Other embodiments are disclosed.

20 Claims, 11 Drawing Sheets

Outside Left Foot View

(51) Int. Cl.
*A61B 5/00* (2006.01)
*G01B 5/02* (2006.01)
*G01B 7/12* (2006.01)
*G01B 7/287* (2006.01)
*A41H 1/02* (2006.01)
*G01B 7/16* (2006.01)

(56) References Cited

U.S. PATENT DOCUMENTS

| | | |
|---|---|---|
| 4,492,234 A | 1/1985 | Arkans |
| 4,501,280 A | 2/1985 | Hood et al. |
| 4,605,010 A | 8/1986 | McEwen |
| 4,770,175 A | 9/1988 | McEwen et al. |
| 5,048,536 A | 9/1991 | McEwen |
| 5,282,467 A | 2/1994 | Piantadosi et al. |
| 5,564,435 A | 10/1996 | Steinberg |
| 5,830,164 A | 11/1998 | Cone et al. |
| 5,991,654 A | 11/1999 | Tumey et al. |
| 6,809,462 B2 | 10/2004 | Eckerle et al. |
| 7,909,849 B2 | 3/2011 | McEwen et al. |
| 9,476,692 B2 | 10/2016 | Reese et al. |
| 2005/0159690 A1 | 7/2005 | Barak et al. |
| 2010/0298920 A1 | 11/2010 | Mrva et al. |
| 2012/0203132 A1 | 8/2012 | Blumensohn et al. |
| 2015/0174396 A1 | 6/2015 | Fisher et al. |
| 2016/0007884 A1 | 1/2016 | Zhu et al. |
| 2016/0015297 A1* | 1/2016 | Strauss ............... A61B 5/4878 600/587 |
| 2016/0038083 A1 | 2/2016 | Ding et al. |
| 2016/0202755 A1 | 7/2016 | Connor |
| 2016/0338644 A1 | 11/2016 | Connor |
| 2017/0079868 A1* | 3/2017 | Reid, Jr. ............. A61B 5/0053 |

FOREIGN PATENT DOCUMENTS

| | | |
|---|---|---|
| WO | 2011134864 A1 | 11/2011 |
| WO | 2014122041 A1 | 8/2014 |
| WO | 2014207653 A1 | 12/2014 |

OTHER PUBLICATIONS

Guttke, S. et al., "Measurement System to determine contraction time of the forearm skeletal muscle", Research and Transfer Center at HTWK, Germany, 2015, 799-803.

Sanders, Joan E. et al., "Assessment of residual-limb volume change using bioimpedence", Journal of rehabilitation research and development 44.4, 2007, 525-536.

* cited by examiner

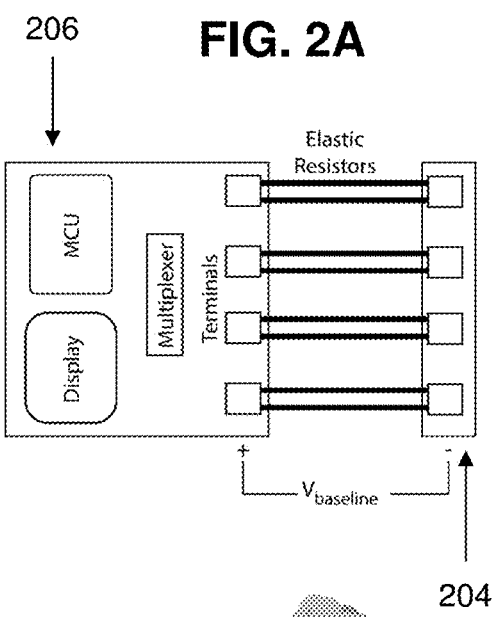
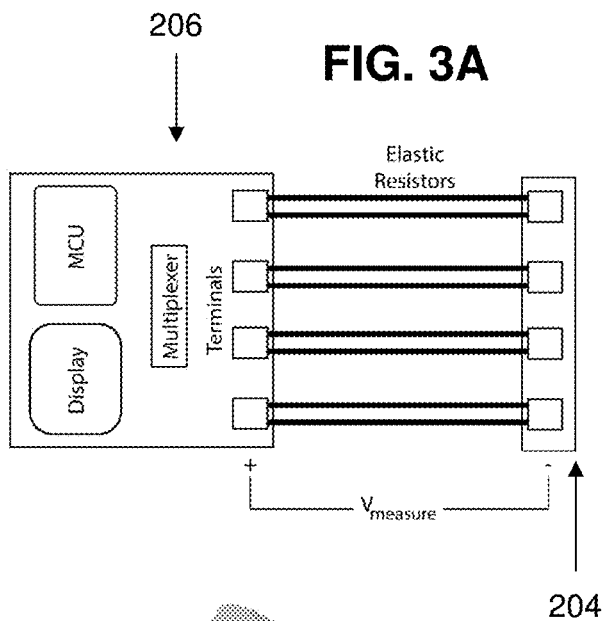
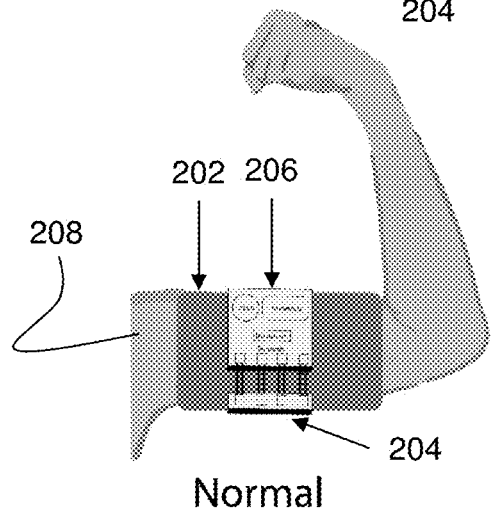
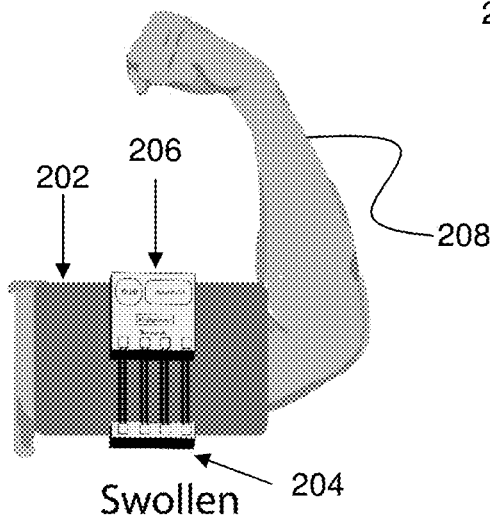
FIG. 2A
FIG. 3A
FIG. 2B
FIG. 3B

400

```
┌─────────────────────────────────────────────────────────────┐
│ Obtaining, from a first elastic measurement element, a first│
│ value representative of a first expanded circumference of a │
│ sleeve at a point in time when the sleeve is disposed on a  │
│ limb of a person                                            │
│ 432                                                         │
└─────────────────────────────────────────────────────────────┘
                              │
                              ▼
┌─────────────────────────────────────────────────────────────┐
│ Obtaining, from a second elastic measurement element, a     │
│ second value representative of a second expanded            │
│ circumference of the sleeve at the point in time when the   │
│ sleeve is disposed on the limb of the person                │
│ 434                                                         │
└─────────────────────────────────────────────────────────────┘
                              │
                              ▼
┌─────────────────────────────────────────────────────────────┐
│ Obtaining, from a third elastic measurement element, a      │
│ third value representative of a third expanded circumference│
│ of the sleeve at the point in time when the sleeve is       │
│ disposed on the limb of the person                          │
│ 436                                                         │
└─────────────────────────────────────────────────────────────┘
                              │
                              ▼
┌─────────────────────────────────────────────────────────────┐
│ Determining, based upon the first value, the second value,  │
│ and the third value, a geometric profile along the length   │
│ of the limb                                                 │
│ 438                                                         │
└─────────────────────────────────────────────────────────────┘
                              │
                              ▼
┌─────────────────────────────────────────────────────────────┐
│        Outputting data representing the geometric profile   │
│                              440                            │
└─────────────────────────────────────────────────────────────┘
```

```
┌─────────────────────────────────────────────────────────────────┐
│ Obtaining a first value representative of a first expanded       │
│ circumference of a sleeve at a point in time when the sleeve is  │
│ disposed on a limb of a person, wherein the first value is       │
│ obtained from a first elastic measurement element that is        │
│ attached to the sleeve at a first location along a length of the │
│ sleeve, the first elastic measurement element traversing a       │
│ portion of the first expanded circumference of the sleeve        │
│                                                            462   │
└─────────────────────────────────────────────────────────────────┘
                                │
                                ▼
┌─────────────────────────────────────────────────────────────────┐
│ Obtaining a second value representative of a second expanded     │
│ circumference of the sleeve at the point in time when the sleeve │
│ is disposed on the limb of the person, wherein the second value  │
│ is obtained from a second elastic measurement element that is    │
│ attached to the sleeve at a second location along the length of  │
│ the sleeve, the second elastic measurement element traversing a  │
│ portion of the second expanded circumference of the sleeve       │
│                                                            464   │
└─────────────────────────────────────────────────────────────────┘
                                │
                                ▼
┌─────────────────────────────────────────────────────────────────┐
│ Obtaining, by the system, a third value representative of a      │
│ third expanded circumference of the sleeve at the point in time  │
│ when the sleeve is disposed on the limb of the person, wherein   │
│ the third value is obtained from a third elastic measurement     │
│ element that is attached to the sleeve at a third location along │
│ the length of the sleeve, the third elastic measurement element  │
│ traversing a portion of the third expanded circumference of the  │
│ sleeve                                                     466   │
└─────────────────────────────────────────────────────────────────┘
                                │
                                ▼
┌─────────────────────────────────────────────────────────────────┐
│ Determining, based upon the first value, the second value, and   │
│ the third value, a geometric profile along the length of the limb│
│                                                            468   │
└─────────────────────────────────────────────────────────────────┘
                                │
                                ▼
┌─────────────────────────────────────────────────────────────────┐
│ Outputting data representing the geometric profile         470   │
└─────────────────────────────────────────────────────────────────┘
```

METHOD AND APPARATUS FOR LIMB CIRCUMFERENCE MEASUREMENT

FIELD OF THE DISCLOSURE

The subject disclosure relates to a method and apparatus for limb circumference measurement.

BACKGROUND

Healthcare professionals sometimes use tape measurements and/or calipers to measure arm and leg circumference. This can be inaccurate and prone to user error (for example, accuracy and errors may depend upon the person performing the measurement and/or the location on the limb where the device is applied).

BRIEF DESCRIPTION OF THE DRAWINGS

Reference will now be made to the accompanying drawings, which are not necessarily drawn to scale, and wherein:

FIGS. 2A, 2B, 3A and 3B depict an illustrative embodiment of an upper arm cuff device;

FIG. 4B depicts an illustrative embodiment of a method used in portions of the systems described in FIGS. 1A, 1B, 2A, 2B, 3A and 3B;

FIG. 4C depicts an illustrative embodiment of a method used in portions of the systems described in FIGS. 1A, 1B, 2A, 2B, 3A and 3B;

DETAILED DESCRIPTION

The subject disclosure describes, among other things, illustrative embodiments for measurement of limb circumference (and/or diameter). Other embodiments are described in the subject disclosure.

One or more aspects of the subject disclosure include a sleeve (for example, in the form of a sock or a cuff) that fits around a limb of a patient. The sleeve can be radially expandable and the sleeve can have therein and/or thereon elastic members that measure a circumference (and/or diameter) of the sleeve at a plurality of locations (thereby determining the circumference (and/or diameter) of the limb at the plurality of locations).

Figures 1A, 1B:
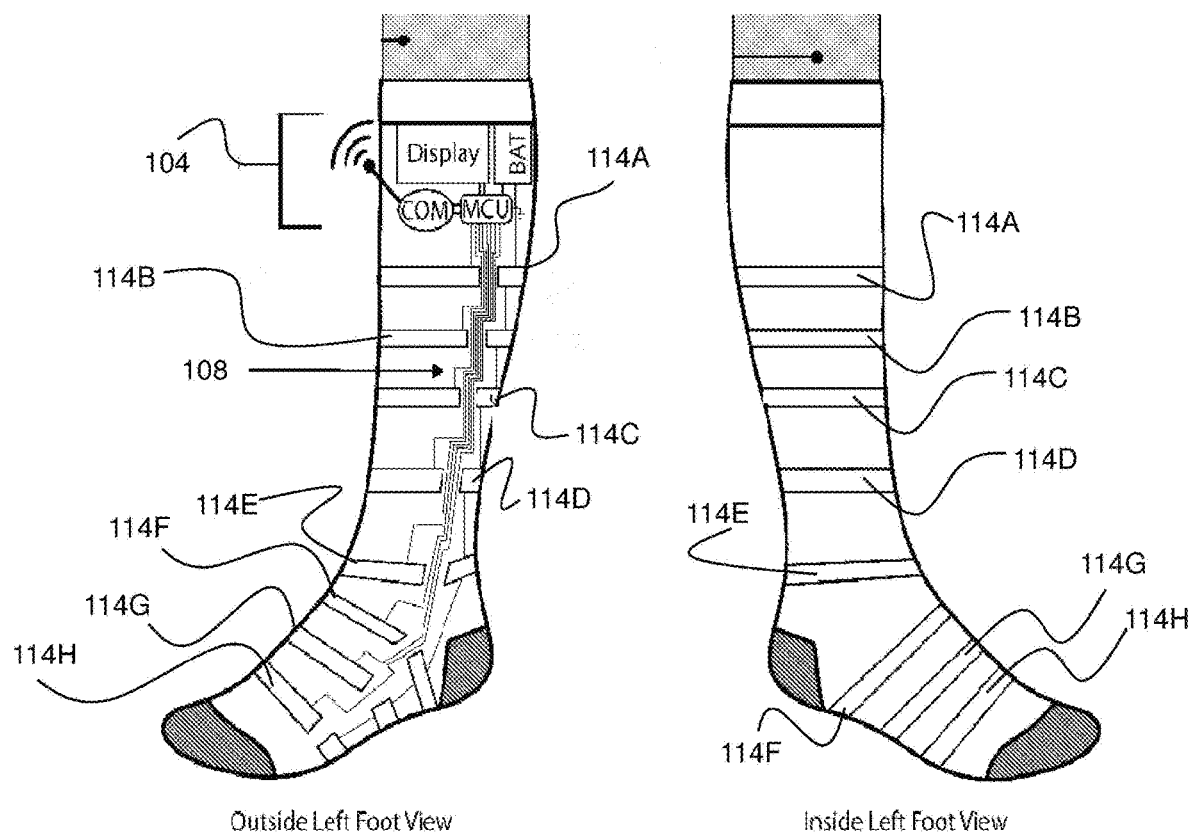
FIGS. 1A and 1B depict an illustrative embodiment of a device for measurements related to a lower leg (FIG. 1A shows an outside left foot view and FIG. 1B shows an inside left foot view)

FIG. 1 depicts an illustrative embodiment of a device used for measuring circumference (and/or diameter) of the lower leg (e.g., foot, ankle and/or calf). In other embodiments, the device can be configured for use on an arm (and/or on other body parts). In the embodiment shown in FIG. 1, a knit fabric sock (e.g., comprising cotton and/or other knit fabrics) contains interwoven conductive knit fabric strips (114A, 114B, 114C, 114D, 114E, 114F, 114G and 114H), conductive thread (shown generally in the figure as 108), and an electronics unit 104. Both the knit fabric and the conductive knit fabric strips (114A-114H) are elastic and pliable. The conductive knit fabric strips (114A-114H) are interwoven into the knit fabric in such a way that each of the conductive knit fabric strips (114A-114H) mostly circumnavigates the lower leg, except for an arc segment (see each of the gaps formed between ends of the conductive knit fabric strips in FIG. 1A). In this example, eight strips of conductive knit fabric are interwoven into the knit fabric (in other examples, any desired number of conductive knit fabric strips may be used). Each arc segment associated with each of the conductive knit fabric strips creates the two poles (high pole for each conductive knit fabric strip and ground pole for each conductive knit fabric strip). Each pair of poles (associated with each conductive knit fabric strip) can be used as points from which to measure the resistance along the respective conductive knit fabric strip. Each arc segment (or gap) also allows for conductive thread (carrying, for example, current associated with a given high pole of a given one of the conductive knit fabric strips) to pass along the length of the sock, to connect the multiple conductive knit fabric strips to the electronics unit. Each of the ground poles of the conductive knit fabric strips may be connected via a ground thread to one another (and to the electronics unit).

The electronics unit 104 comprises a microcontroller unit (MCU), a communication module (COM), a display (e.g., an organic light-emitting diode (OLED)), and a battery. The MCU can be capable of processing multiple analog channels (in this example, eight would be used). In another example, the MCU can work in conjunction with an analog multiplexer chip. In other examples, higher or lower number of analog channels can be used. Along with the MCU, multiple internal resistors are connected in series with the conductive knit fabric strips (e.g., one resistor per strip), in order to create a voltage divider. The COM can be of any desired communication protocol, for example, BLE (Bluetooth Low Energy), WIFI, and/or LTE (Long-Term Evolution). The COM can transmit the measurements from the MCU to a remote device (e.g., a mobile or a stationary device) and/or to the cloud (e.g., via the Internet) for further analysis, display and/or storage. The display of the electronics unit 104 can show calculated circumference values (e.g., in response to triggers from the MCU). The battery (BAT), can power the MCU, the display, and COM, as well as provide the voltage differential between each high and ground pole of a respective conductive knit fabric strip, along the voltage divider with the internal resistors.

As the leg morphology changes, each conductive knit fabric strip will expand or compress around the leg. As the conductive knit fabric strips change in dimension, they will report different resistance values. The MCU will interpret these resistance value changes into changes in circumference at the location of each conductive knit fabric strip. The multiple circumference values along the length of the sock can give insight into the limb's morphology changes in response to (for example) swelling, leg movements, or other differential measurements. Increasing the number of conductive knit fabric strips can give higher resolution representations of leg morphology.

Referring now to FIGS. 2A, 2B, 3A and 3B, a cuff device 202 (comprising measurement unit 206) is shown in its baseline (or normal) state (see FIGS. 2A and 2B) and in its measurement (or swollen) state (see FIGS. 3A and 3B). As seen, the cuff device 202 is configured for placement on an arm 208 of a patient. The cuff device 202 utilizes resistive elastomers (see the four elements in FIG. 2A depicted as horizontal bars, the four elements in FIG. 2B depicted as vertical bars, the four elements in FIG. 3A depicted as horizontal bars and the four elements in FIG. 3B depicted as vertical bars). The elastomers change their resistance as they are being extended and relaxed. The change in resistance can be correlated to extent of extension. A number of elastic resistors are connected in parallel in order to obtain extent of extension at multiple points along a limb (that is, along arm 208 in FIGS. 2B and 3B). In FIGS. 2B and 3B use on an upper arm is shown. In other embodiments, the device can be configured for use on a leg (and/or on other body parts). The elastic resistors will stretch in response to swelling of the upper arm. The amount of swelling can be correlated to the extent of extension in each elastomer by creating a profile (e.g., correlating limb size to elastomer extension). The circumference value around the limb (upper arm in this example) is determined (e.g., estimated) from each elastomer's measured extension value. The circumference values create a geometrical profile along the limb (in this example, the upper arm). In one example, each of the resistive elastomers can be anchored at a first end to measurement unit 206 and at a second end to anchor member 204. The anchoring arrangement can permit placement of the ends of the resistive elastomers at appropriate locations to provide a desired amount of extension/contraction and/or to permit measurement of larger or smaller limbs.

Figure 4A:
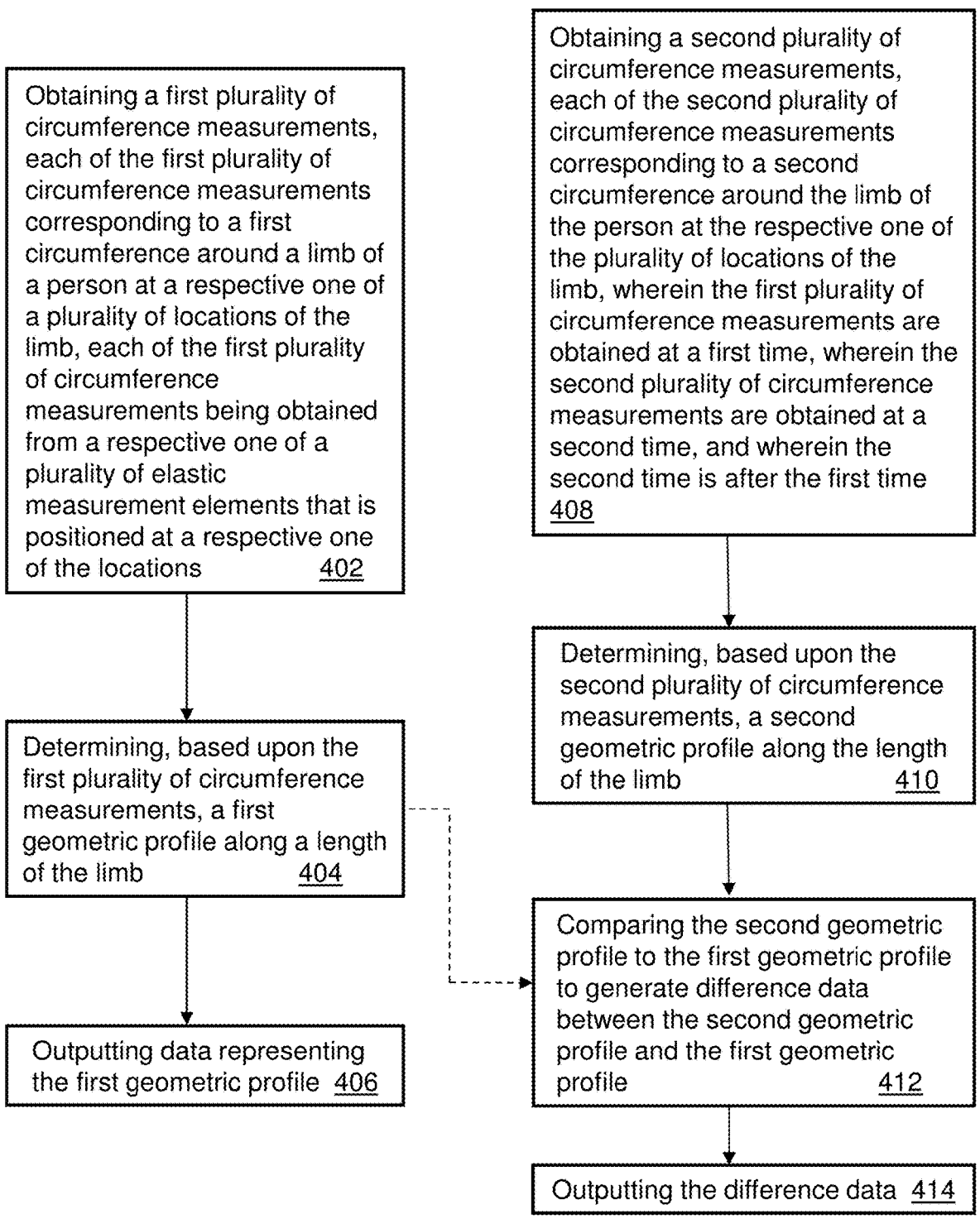
FIG. 4A depicts an illustrative embodiment of a method used in portions of the systems described in FIGS. 1A, 1B, 2A, 2B, 3A and 3B.

FIG. 4A depicts an illustrative embodiment of a method used in portions of the systems described in FIGS. 1A, 1B, 2A, 2B, 3A and 3B. While for purposes of simplicity of explanation, the respective processes are shown and described as a series of blocks in FIG. 4A, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Still referring to FIG. 4A, method 400 begins at step 402 with obtaining a first plurality of circumference measurements, each of the first plurality of circumference measurements corresponding to a first circumference around a limb of a person at a respective one of a plurality of locations of the limb, each of the first plurality of circumference measurements being obtained from a respective one of a plurality of elastic measurement elements that is positioned at a respective one of the locations. Method 400 then continues at step 404 with determining, based upon the first plurality of circumference measurements, a first geometric profile along a length of the limb. Method 400 then continues at step 406 with outputting data representing the first geometric profile.

Still referring to FIG. 4A, method 400 can include step 408, of obtaining a second plurality of circumference measurements, each of the second plurality of circumference measurements corresponding to a second circumference around the limb of the person at the respective one of the plurality of locations of the limb, wherein the first plurality of circumference measurements are obtained at a first time, wherein the second plurality of circumference measurements are obtained at a second time, and wherein the second time is after the first time. This branch of method 400 then continues at step 410 with determining, based upon the second plurality of circumference measurements, a second geometric profile along the length of the limb. This branch of method 400 then continues at step 412 with comparing the second geometric profile to the first geometric profile to generate difference data between the second geometric profile and the first geometric profile (as seen by the dashed line in FIG. 4A, the first geometric profile can be obtained at step 412 from step 404). This branch of method 400 then continues at step 414 with outputting the difference data.

FIG. 4B depicts an illustrative embodiment of a method used in portions of the systems described in FIGS. 1A, 1B, 2A, 2B, 3A and 3B. While for purposes of simplicity of explanation, the respective processes are shown and described as a series of blocks in FIG. 4B, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Still referring to FIG. 4B, method 430 begins at step 432 with obtaining, from a first elastic measurement element, a first value representative of a first expanded circumference of a sleeve at a point in time when the sleeve is disposed on a limb of a person. Method 430 then continues at step 434 with obtaining, from a second elastic measurement element, a second value representative of a second expanded circumference of the sleeve at the point in time when the sleeve is disposed on the limb of the person. Method 430 then continues at step 436 with obtaining, from a third elastic measurement element, a third value representative of a third expanded circumference of the sleeve at the point in time when the sleeve is disposed on the limb of the person. Method 430 then continues at step 438 with determining, based upon the first value, the second value, and the third value, a geometric profile along the length of the limb. Method 430 then continues at step 440 with outputting data representing the geometric profile.

FIG. 4C depicts an illustrative embodiment of a method used in portions of the systems described in FIGS. 1A, 1B, 2A, 2B, 3A and 3B. While for purposes of simplicity of explanation, the respective processes are shown and described as a series of blocks in FIG. 4C, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Still referring to FIG. 4C, method 460 begins at step 462 with obtaining a first value representative of a first expanded circumference of a sleeve at a point in time when the sleeve is disposed on a limb of a person, wherein the first value is obtained from a first elastic measurement element that is attached to the sleeve at a first location along a length of the sleeve, the first elastic measurement element traversing a portion of the first expanded circumference of the sleeve. Method 460 then continues at step 464 with obtaining a second value representative of a second expanded circumference of the sleeve at the point in time when the sleeve is disposed on the limb of the person, wherein the second value is obtained from a second elastic measurement element that is attached to the sleeve at a second location along the length of the sleeve, the second elastic measurement element traversing a portion of the second expanded circumference of the sleeve. Method 460 then continues at step 466 with obtaining a third value representative of a third expanded circumference of the sleeve at the point in time when the sleeve is disposed on the limb of the person, wherein the third value is obtained from a third elastic measurement element that is attached to the sleeve at a third location along the length of the sleeve, the third elastic measurement element traversing a portion of the third expanded circumference of the sleeve. Method 460 then continues at step 468 with determining, based upon the first value, the second value, and the third value, a geometric profile along the length of the limb. Method 460 then continues at step 470 with outputting data representing the geometric profile.

Figure 5:
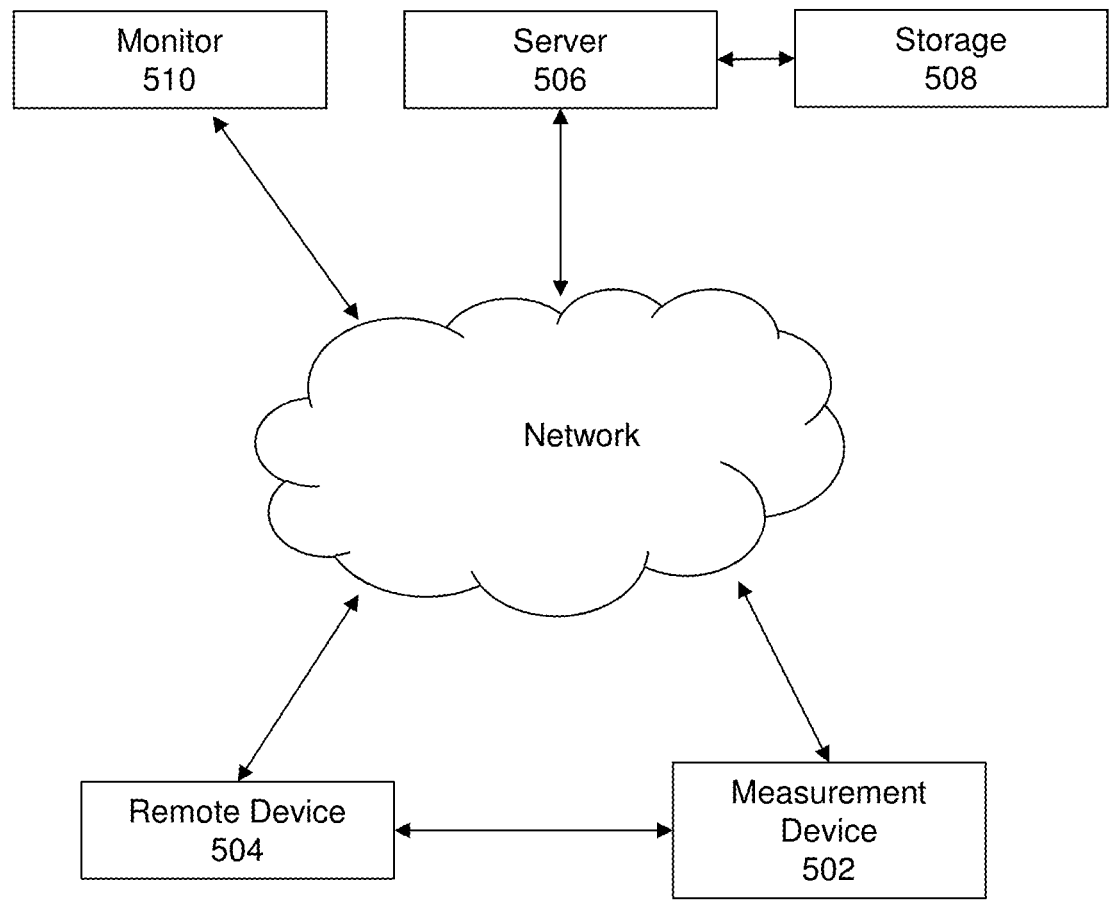
FIG. 5 depicts an illustrative embodiment of a system that can be used in the context of obtaining, displaying and storing measurements.

Referring now to FIG. 5, depicted is an illustrative embodiment of a system 500 that can be used in the context of obtaining, displaying and storing measurements. As seen, measurement device 502 (such as a sleeve, sock or cuff as described herein) can be in communication with remote device 504 (in this example, the remote device 504 is remote in the sense that it is a different device than measurement device 502; the remote device 504 could, for example, be used in the same room as measurement device 502 or in a different room and/or a different building). The communication with remote device 504 can be bi-directional communication. The communication with remote device 504 can comprise wireless communication (e.g., BLE, WIFI, and/or LTE). The remote device 504 can be a tablet, a laptop computer, a desktop computer and/or another mobile device such as a smartphone. Remote device 504 can display on a display screen thereof data provided from the measurement device 502. Remote device 504 can provide operating instructions to measurement device 502. Remote device 504 can receive one or more alerts (e.g., alerts relating to measured values and/or measurement parameters) from measurement device 502.

Still referring to FIG. 5, measurement device 502 can be in communication with server 506. The communication with server 506 can be via a network (e.g., the Internet). The communication with server 506 can be bi-directional communication. The communication with server 506 can comprise wireless communication (e.g., Ethernet, WIFI, and/or LTE). The communication with server 506 can be web-based. The measurement device 502 can provide to server 506 measurement data. Server 506 can display on a display screen thereof the measurement data from the measurement device 502. Server 506 can provide operating instructions to measurement device 502. Server 506 can be in communication (e.g., bi-directional communication) with storage 508 (e.g., disk storage and/or solid-state storage). Storage 508 can store thereon measurement data received by server 506.

Still referring to FIG. 5, remote device 504 can be in communication with server 506. The communication with server 506 can be via a network (e.g., the Internet). The communication with server 506 can be bi-directional communication. The communication with server 506 can comprise wireless communication (e.g., Ethernet, WIFI, and/or LTE). The communication with server 506 can be web-based. The remote device 504 can provide to server 506 measurement data (e.g., measurement data that had been received by remote device 504 from measurement device 502). Server 506 can display on a display screen thereof the measurement data received from the remote device 504. Server 506 can provide operating instructions to remote device 504.

Still referring to FIG. 5, monitor 510 can be in communication with server 506. Monitor 510 can be any device that provides graphical output (e.g., a computer and/or computer system). The communication with server 506 can be via a network (e.g., the Internet). The communication with server 506 can be bi-directional communication. The communication with server 506 can comprise wireless communication (e.g., Ethernet, WIFI, and/or LTE). The communication with server 506 can be web-based. The monitor 510 can receive from server 506 measurement data. In one specific example, the measurement data received by monitor 510 can be in the form of an aggregated data set comprising data from a plurality of (e.g., all) patients. Monitor 510 can display on a display screen thereof the data set (e.g., in graphical form).

In one embodiment, the monitor 510 can provide the ability for a clinician to view data from a specific measurement device (e.g., selected from a plurality of measurement devices), pulled from the server 506 in real-time and/or through storage 508. In one embodiment, the monitor 510 can be used for visualization of the data in graph/table form.

Figure 6A:
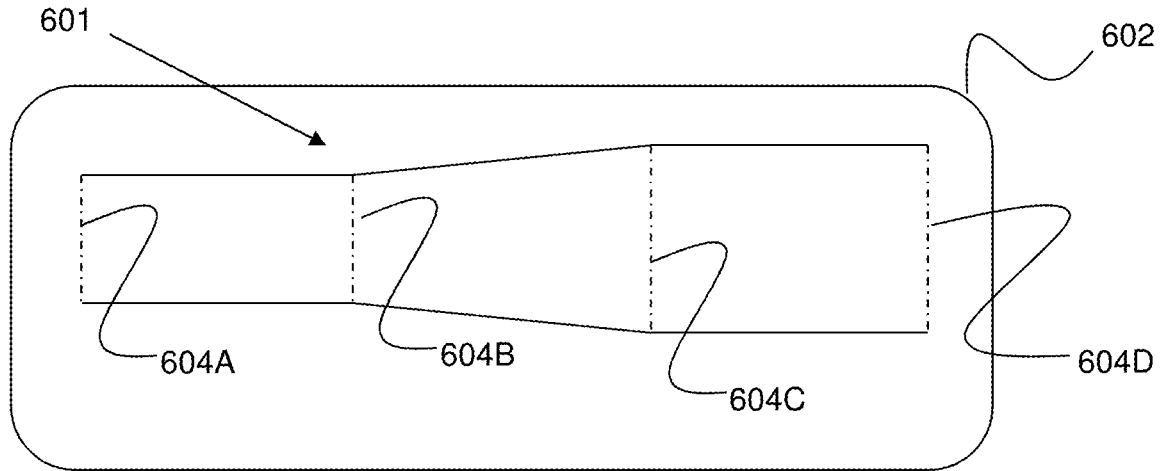
FIGS. 6A, 6B and 6C depict illustrative embodiments of a geometric profile of a limb of a person as presented on a display.

Referring now to FIG. 6A, a display 602 (e.g., on a computer monitor, a tablet or the like) presents a geometric profile 601 of a limb of a person. The geometric profile 601 is defined by distances 604A, 604B, 604C and 604D (see the dashed lines in FIG. 6A). Each of distances 604A, 604B, 604C and 604D had been measured by a measurement element (e.g., an elastic measurement element) located on (and/or in) a sleeve or the like as described herein. The location of each of distances 604A, 604B, 604C and 604D corresponds to a respective location on the limb of the person.

Figure 6B:
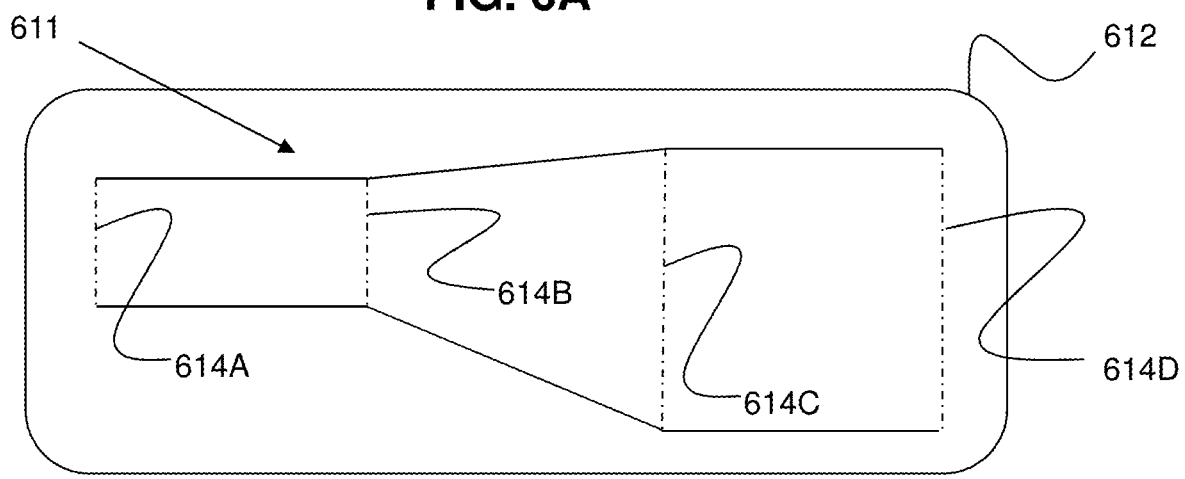

Referring now to FIG. 6B, a display 612 (e.g., on a computer monitor, a tablet or the like) presents a geometric profile 611 of a limb of a person. The geometric profile 611 is defined by distances 614A, 614B, 614C and 614D (see the dashed lines in FIG. 6B). Each of distances 614A, 614B, 614C and 614D had been measured by a measurement element (e.g., an elastic measurement element) located on (and/or in) a sleeve or the like as described herein. The location of each of distances 614A, 614B, 614C and 614D corresponds to a respective location on the limb of the person. In one embodiment, the measurements for geometric profile 601 had been taken at a first point in time and the measurements for geometric profile 611 had been taken at a second point in time that is different from the first point in time. For example, the first point in time could have been a particular day, and the second point in time could have been a certain number of days, weeks, or months later. In another example, the first point in time could have been a particular hour, and the second point in time could have been a certain number of hours later. In another example, the first point in time could have been a particular minute, and the second point in time could have been a certain number of minutes later.

Figure 6C:
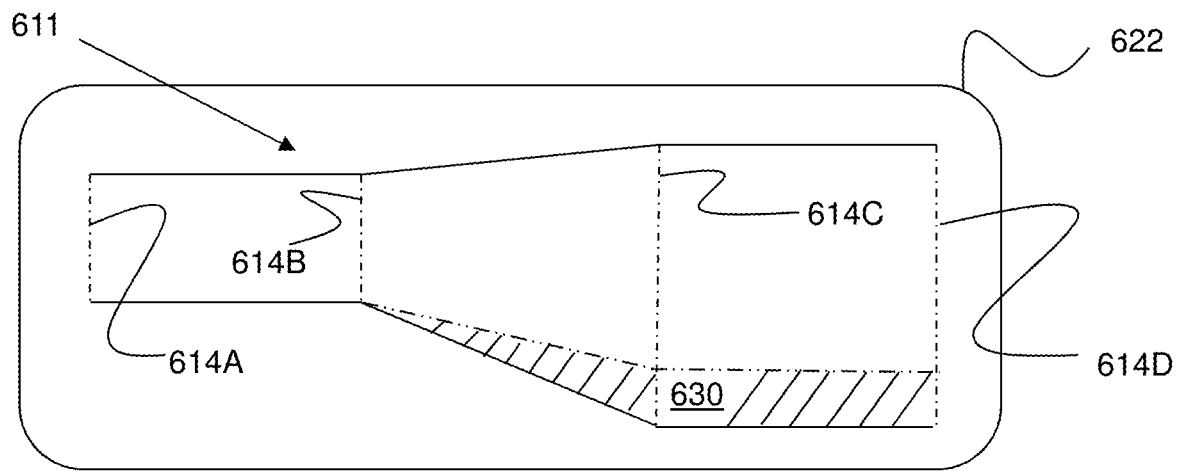

Referring now to FIG. 6C, a display 622 (e.g., on a computer monitor, a tablet or the like) presents the geometric profile 611 (see FIG. 6B) of the limb of the person. The geometric profile 611 in this FIG. 6C is again defined by distances 614A, 614B, 614C and 614D (see the dashed lines in FIG. 6C). The geometric profile 611 includes, in the presentation of FIG. 6C, a shaded area 630 that identifies the difference between geometric profile 611 and geometric profile 601. In this example, geometric profile 611 includes the additional area 630 that is not included in geometric profile 601. In other examples, the second geometric profile may be smaller than the first geometric profile. Further, in other examples, the first and second geometric profiles can have different shapes.

Figure 7A:
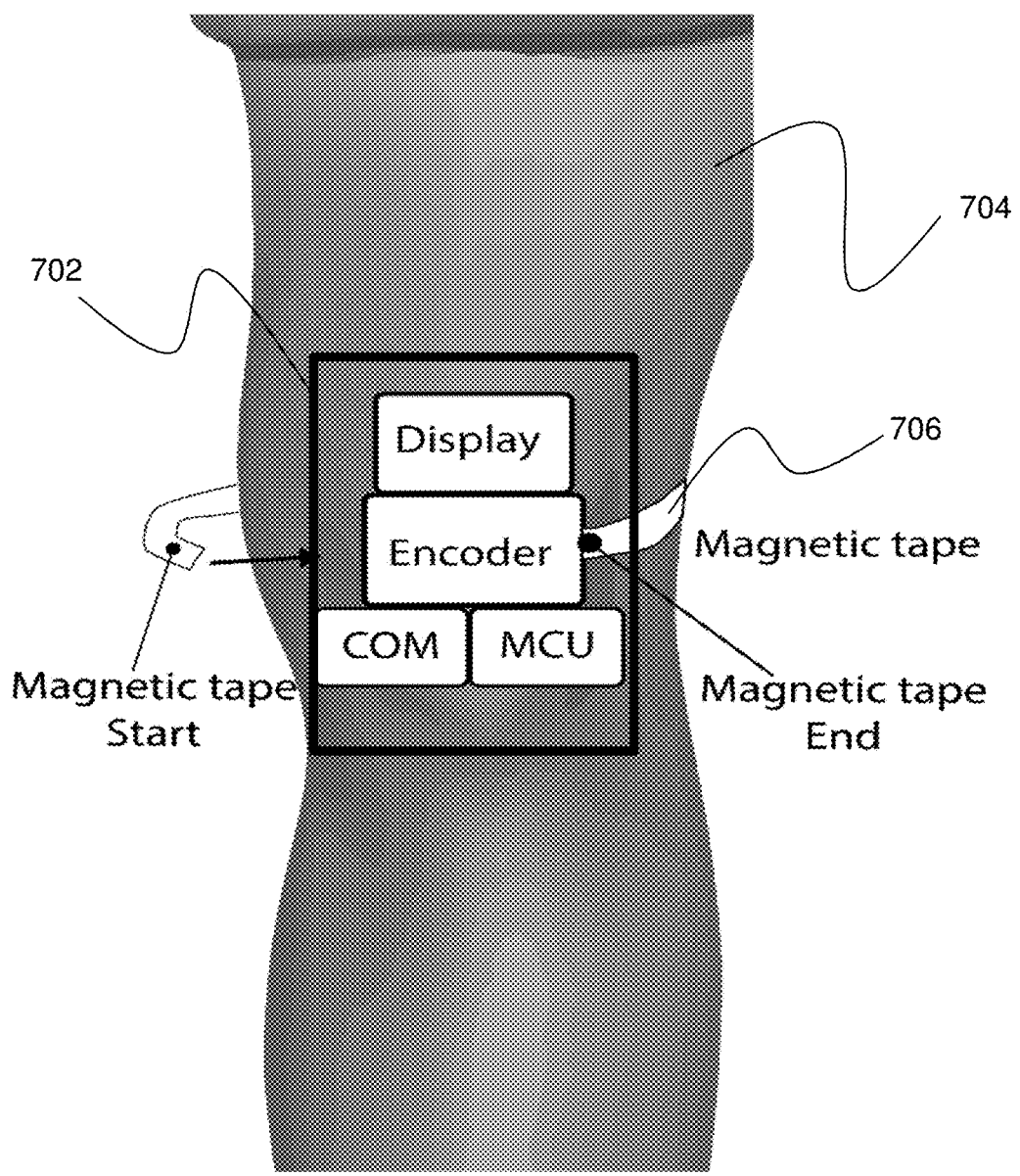
FIGS. 7A and 7B depict illustrative embodiments of measurement devices.

Referring now to FIG. 7A, measurement device 702 operates as an electronic version of a tape measure. The measurement device 702 uses a flexible magnetically encoded tape 706 and an encoder. A tool that is sometimes used in an industrial setting (to measure accurate displacement) is typically utilized by traversing an encoder along a fixed tape. For limb circumference measurement as described herein, the application could be reversed, to where the magnetically encoded tape 706 moves along a fixed encoder. The magnetically encoded tape 706 can be on a reel inside the device (similar to a standard tape measure). As the magnetically encoded tape 706 is pulled out of the reel, the magnetically encoded tape 706 slides along the encoder. As the magnetically encoded tape 706 is wrapped around the limb (and is contacted to (and/or connected with)) the opposite side of the measurement device 702, the encoder keeps track of the amount of magnetically encoded tape 706 that has passed. As the magnetically encoded tape 706 contacts (and/or connects with) the opposite side of the device, a circumference value is interpreted by the MCU (microcontroller unit), based on the length of magnetically encoded tape 706 that has passed along the encoder. The measurement value is then displayed and/or sent over the COM (communication module) to a remote device and/or to the cloud.

Figure 7B:
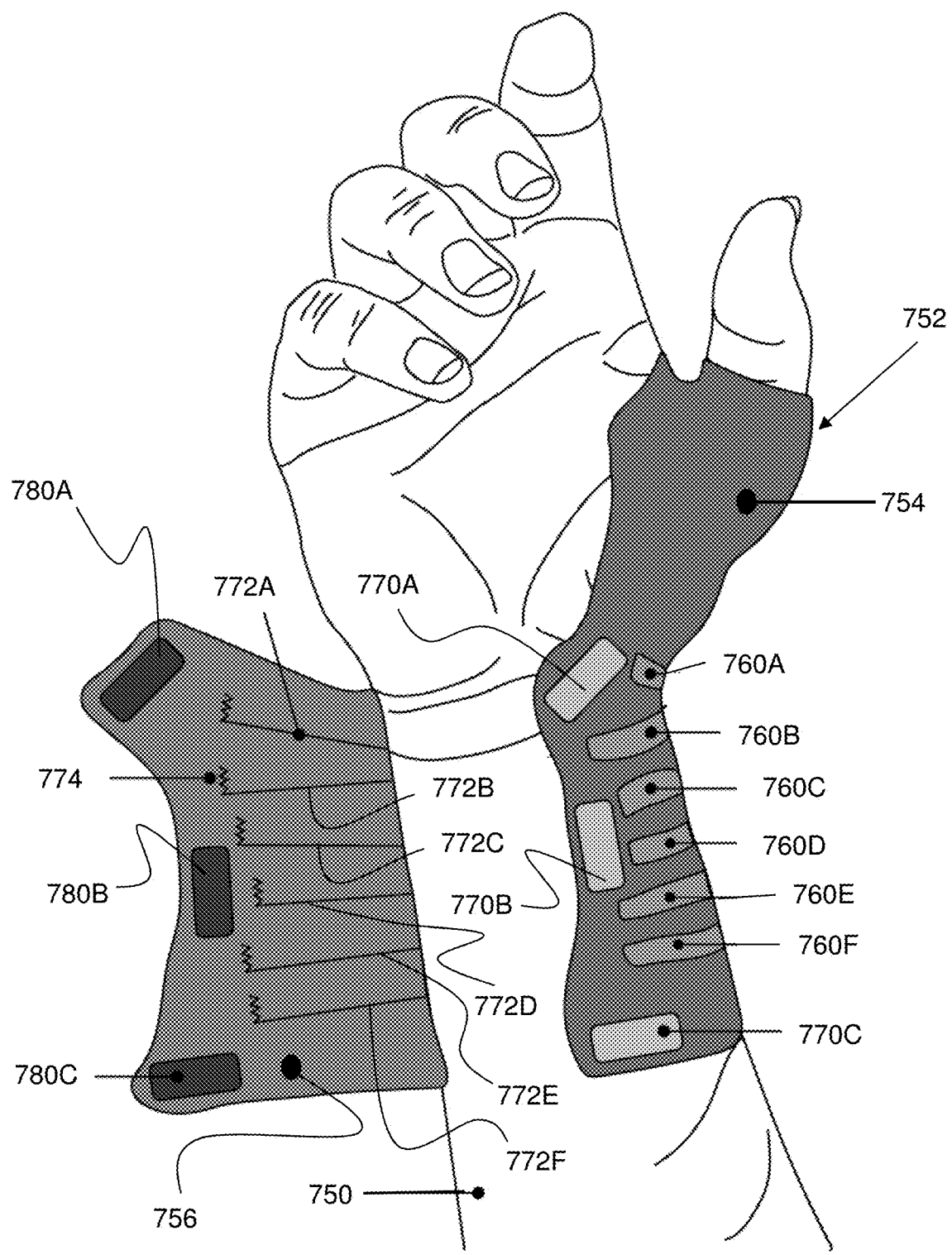

Referring now to FIG. 7B, depicted is an illustrative embodiment of a device 752 used for measuring circumference (and/or diameter) of the arm 750 (e.g., in the area of the wrist and forearm). In other embodiments, the device can be configured for use on a leg (and/or on other body parts). In the embodiment shown in FIG. 7B, a knit cuff (e.g., comprising cotton and/or other knit fabrics) contains elastic conductive strips (760A, 760B, 760C, 760D, 760E, 760F). The elastic conductive strips (760A, 760B, 760C, 760D, 760E, 760F) are located on a top (or outer) layer 754 of device 752. A corresponding plurality of conductive threads (or traces) are located on a bottom (or inner) layer 756 of device 752. The conductive threads are identified in FIG. 7B as 772A, 772B, 772C, 772D, 772E, 772F. Each of conductive threads 772A, 772B, 772C, 772D, 772E, 772F is stitched (through the device 752 to top layer 754) to a first pole of a corresponding one of the elastic conductive strips 760A, 760B, 760C, 760D, 760E, 760F. Each of a plurality of other conductive threads (not shown) are stitched (through the device 752 to top layer 754) to a second pole of a corresponding one of the elastic conductive strips 760A, 760B, 760C, 760D, 760E, 760F. Call out number 774 shows one such stitching between conductive thread 772B and elastic conductive strip 760B (the remaining stitches shown in FIG. 7B are not provided with call out numbers). The conductive threads thus provide electrical conductive paths from each of the poles of the elastic conductive strips to various electrical components (such as, for example, those shown in FIGS. 1A, 1B, 2A, 2B, 3A, 3B and 7A). Hook-and-loop fastener loop portions 780A, 780B, 780C are attachable to corresponding hook-and-loop fastener hook portions 770A, 770B, 770C to firmly attach the device 752 to the person's hand/arm.

In one specific example, using a multiple layer configuration (e.g., with elastic conductive strips on one side and conductive threads on another side) may be useful where a very small gap is provided between each end (or pole) of a particular elastic conductive strip (thus rendering the running of the conductive threads through the gap as difficult).

As the arm morphology changes, each elastic conductive strip will expand or compress around the arm. As the elastic conductive strips change in dimension, they will report different resistance values. The electronics will interpret these resistance value changes into changes in circumference at the location of each elastic conductive strip. The multiple circumference values along the length of the arm can give insight into the limb's morphology changes in response to (for example) swelling, arm movements, or other differential measurements. Increasing the number of elastic conductive strips can give higher resolution representations of arm morphology.

In various embodiments, n number of measurement elements can be used to collect data from n number of locations along a limb. In one specific example, n can be an integer between 2 and 50 (inclusive). In one specific example, the distance between each of the n number of adjacent measurement elements along the device can be a known or fixed distance (e.g., 0.5 inch). In another example, a device can be provided in multiple sizes (e.g., child and adult or small, medium and large). In one specific example, the spacing between measurement elements across sizes can be constant, with the number of measurement elements being higher for larger sizes (e.g., a child size device can be 5 inches long, use 5 measurement elements and have each adjacent measurement element spaced 1 inch apart, while the corresponding adult size device can be 10 inches long, use 10 measurement elements and have each adjacent measurement element spaced 1 inch apart). Decreasing the spacing between adjacent measurement elements can increase measurement resolution.

As described herein, various embodiments provide a device for measuring body parts such as, for example: fingers (e.g., circumference and/or diameter); arms (e.g., circumference and/or diameter); legs (e.g., circumference and/or diameter); feet (e.g., circumference and/or diameter); and/or toes (e.g., circumference and/or diameter). In one specific example, a circumference and/or diameter of the upper arm in the area of the triceps/biceps can be measured. In another specific example, a circumference and/or diameter of the lower arm in the area of the forearm can be measured. In another specific example, a circumference and/or diameter of the upper leg in the area of the thigh can be measured. In another specific example, a circumference and/or diameter of the lower leg in the area of the calf can be measured. In another specific example, a circumference and/or diameter of the neck can be measured.

As described herein, various embodiments provide a device comprising a number of elastic members, whereby stretching of each elastic member changes electrical properties which can be measured by the device.

As described herein, various embodiments provide a sleeve, a sock, a cuff, or the like to fit over a body part and elastic resistors (and/or other elastic material) supported by the sleeve, sock, cuff, or the like (in or on) that can be stretched and the stretching can be measured via changes to electrical properties so that the body part can be measured, such as a circumference of a calf or arm to detect swelling. The measurements can be provided to a display on the device, to a nurse's or doctor's tablet and/or to the cloud. In one example, resistance measurements can be used. In other examples, other electrical (and/or mechanical) properties that change when a material is stretched can be measured and used for the circumference (and/or diameter) determinations.

In one embodiment, the elastic members are removable (and/or disposable) so that a number of uses and age of material does not affect the measurement capabilities (e.g., does not affect the accuracy or repeatability of the measurements). In one embodiment, the sleeve, sock, cuff, or the like and the elastic resistors can be adjustable to fit smaller or larger body parts, such as elastic resistors which can be adjusted as to a point of connection to the sleeve, sock, cuff, or the like (e.g., point of connection on the elastic resistor and/or point of connection on the sleeve, sock, cuff, or the like).

As described herein is a limb measurement tool that, in various embodiments, uses multiple fixed (or predetermined) locations to give an accurate measurement of, for example, arm or leg circumference (and/or diameter).

By using a series of elastic resistors an ability to gather accurate measurement of arm or leg circumference (and/or diameter) is provided. The resistors can be placed inside a compressed sleeve that is placed on a patient's arm or leg. In one specific example, the patient puts the sleeve on his or her arm or leg and presses a button on the device, which calculates the measurement and then transmits the measurement securely into the cloud and/or to an electronic health record associated with the patient.

In another embodiment, a sleeve may be of a planar form, such that the sleeve can be rolled around the limb to form a cylindrical shape (similar to a typical blood pressure cuff). In one specific example, the rolled sleeve may be maintained in the cylindrical form using hook-and-loop fasteners, clips, snaps or the like.

In various embodiments, one or more statistical metrics can be calculated and/or output (e.g., to a display and/or to a storage). The storage can be, for example, on the cloud and/or in an electronic health record associated with the patient.

In another embodiment, the statistical metric can be output via an audio speaker.

In one example, the statistical metric comprises one of an arithmetic mean of first and second values (e.g., first and second circumference values and/or first and second diameter values), a range of the first and second values (e.g., first and second circumference values and/or first and second diameter values), or both.

In one example, the statistical metric comprises one of an arithmetic mean of a set of values (e.g., a set of circumference values and/or a set of diameter values), a mode of the set of values (e.g., a set of circumference values and/or a set of diameter values), a median of the set of values (e.g., a set of circumference values and/or a set of diameter values), a range of the set of values (e.g., a set of circumference values and/or a set of diameter values), or any combination thereof.

As described herein, various embodiments provide a method of continuously measuring limb circumference to monitor signs of inflammation.

In one embodiment, the electronic components used to sample from the multiple channels of elastic measurement elements can comprise analog multiplexers and/or shift registers.

In one embodiment, developer debugging may be provided (e.g., via a server such as server 506 of FIG. 5).

Figure 8:
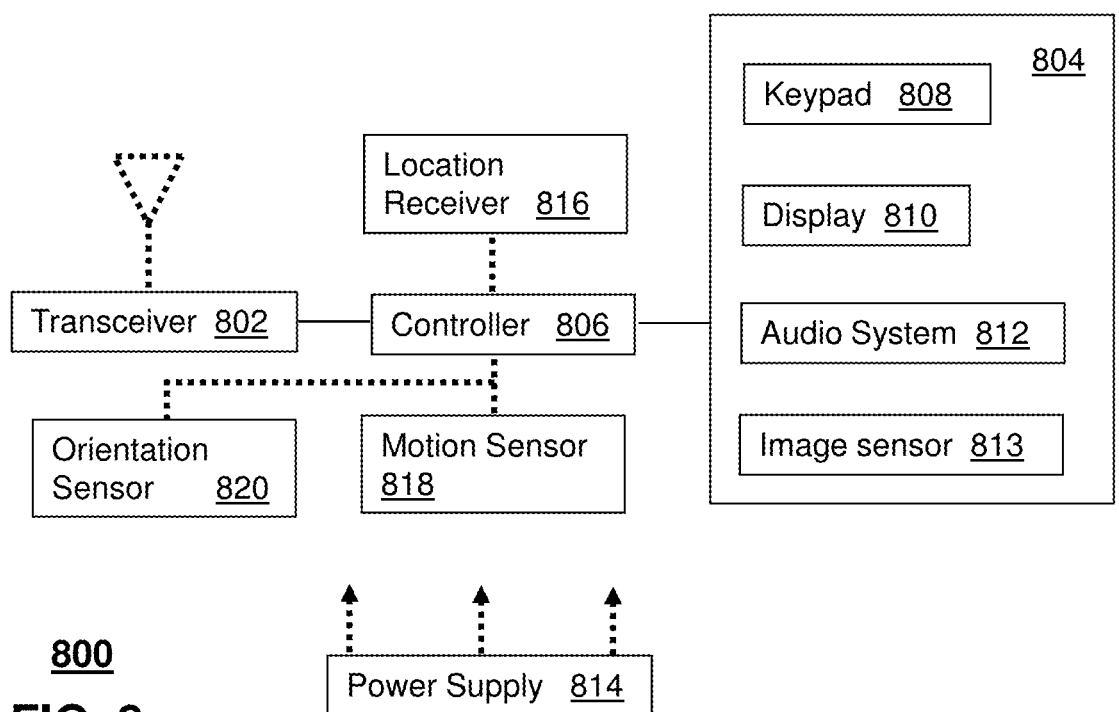
FIG. 8 depicts an illustrative embodiment of a communication device.

FIG. 8 depicts an illustrative embodiment of a communication device 800. Communication device 800 can serve in whole or in part as an illustrative embodiment of the devices depicted in FIGS. 1A, 1B, 2A, 2B, 3A, 3B, 5, 7A and/or 7B and can be configured to perform portions of methods 400, 430 and/or 460 of FIGS. 4A-4C.

Communication device 800 can comprise a wireline and/or wireless transceiver 802 (herein transceiver 802), a user interface (UI) 804, a power supply 814, a location receiver 816, a motion sensor 818, an orientation sensor 820, and a controller 806 for managing operations thereof. The transceiver 802 can support short-range or long-range wireless access technologies such as Bluetooth®, ZigBee®, WiFi, DECT, or cellular communication technologies, just to mention a few (Bluetooth® and ZigBee® are trademarks registered by the Bluetooth® Special Interest Group and the ZigBee® Alliance, respectively). Cellular technologies can include, for example, CDMA-1X, UMTS/HSDPA, GSM/GPRS, TDMA/EDGE, EV/DO, WiMAX, SDR, LTE, as well as other next generation wireless communication technologies as they arise. The transceiver 802 can also be adapted to support circuit-switched wireline access technologies (such as PSTN), packet-switched wireline access technologies (such as TCP/IP, VoIP, etc.), and combinations thereof.

The UI 804 can include a depressible or touch-sensitive keypad 808 with a navigation mechanism such as a roller ball, a joystick, a mouse, or a navigation disk for manipulating operations of the communication device 800. The keypad 808 can be an integral part of a housing assembly of the communication device 800 or an independent device operably coupled thereto by a tethered wireline interface (such as a USB cable) or a wireless interface supporting for example Bluetooth®. The keypad 808 can represent a numeric keypad commonly used by phones, and/or a QWERTY keypad with alphanumeric keys. The UI 804 can further include a display 810 such as monochrome or color LCD (Liquid Crystal Display), OLED (Organic Light Emitting Diode) or other suitable display technology for conveying images to an end user of the communication device 800. In an embodiment where the display 810 is touch-sensitive, a portion or all of the keypad 808 can be presented by way of the display 810 with navigation features.

The display 810 can use touch screen technology to also serve as a user interface for detecting user input. As a touch screen display, the communication device 800 can be adapted to present a user interface with graphical user interface (GUI) elements that can be selected by a user with a touch of a finger. The touch screen display 810 can be equipped with capacitive, resistive or other forms of sensing technology to detect how much surface area of a user's finger has been placed on a portion of the touch screen display. This sensing information can be used to control the manipulation of the GUI elements or other functions of the user interface. The display 810 can be an integral part of the housing assembly of the communication device 800 or an independent device communicatively coupled thereto by a tethered wireline interface (such as a cable) or a wireless interface.

The UI 804 can also include an audio system 812 that utilizes audio technology for conveying low volume audio (such as audio heard in proximity of a human ear) and high volume audio (such as speakerphone for hands free operation). The audio system 812 can further include a microphone for receiving audible signals of an end user. The audio system 812 can also be used for voice recognition applications. The UI 804 can further include an image sensor 813 such as a charged coupled device (CCD) camera for capturing still or moving images.

The power supply 814 can utilize common power management technologies such as replaceable and rechargeable batteries, supply regulation technologies, and/or charging system technologies for supplying energy to the components of the communication device 800 to facilitate long-range or short-range portable applications. Alternatively, or in combination, the charging system can utilize external power sources such as DC power supplied over a physical interface such as a USB port or other suitable tethering technologies.

The location receiver 816 can utilize location technology such as a global positioning system (GPS) receiver capable of assisted GPS for identifying a location of the communication device 800 based on signals generated by a constellation of GPS satellites, which can be used for facilitating location services such as navigation. The motion sensor 818 can utilize motion sensing technology such as an accelerometer, a gyroscope, or other suitable motion sensing technology to detect motion of the communication device 800 in three-dimensional space. The orientation sensor 820 can utilize orientation sensing technology such as a magnetometer to detect the orientation of the communication device 800 (north, south, west, and east, as well as combined orientations in degrees, minutes, or other suitable orientation metrics).

The communication device 800 can use the transceiver 802 to also determine a proximity to a cellular, WiFi, Bluetooth®, or other wireless access points by sensing techniques such as utilizing a received signal strength indicator (RSSI) and/or signal time of arrival (TOA) or time of flight (TOF) measurements. The controller 806 can utilize computing technologies such as a microprocessor, a digital signal processor (DSP), programmable gate arrays, application specific integrated circuits, and/or a video processor with associated storage memory such as Flash, ROM, RAM, SRAM, DRAM or other storage technologies for executing computer instructions, controlling, and processing data supplied by the aforementioned components of the communication device 800.

Other components not shown in FIG. 8 can be used in one or more embodiments of the subject disclosure. For instance, the communication device 800 can include a reset button (not shown). The reset button can be used to reset the controller 806 of the communication device 800. In yet another embodiment, the communication device 800 can also include a factory default setting button positioned, for example, below a small hole in a housing assembly of the communication device 800 to force the communication device 800 to re-establish factory settings. In this embodiment, a user can use a protruding object such as a pen or paper clip tip to reach into the hole and depress the default setting button. The communication device 800 can also include a slot for adding or removing an identity module such as a Subscriber Identity Module (SIM) card. SIM cards can be used for identifying subscriber services, executing programs, storing subscriber data, and so forth.

The communication device 800 as described herein can operate with more or less of the circuit components shown in FIG. 8. These variant embodiments can be used in one or more embodiments of the subject disclosure. The communication device 800 can be adapted to perform the functions of electronics unit 104, measurement unit 206, measurement device 502, remote device 504, server 506 and/or measurement device 702. It will be appreciated that the communication device 800 can also represent other devices that can operate in systems described herein.

Upon reviewing the aforementioned embodiments, it would be evident to an artisan with ordinary skill in the art that said embodiments can be modified, reduced, or enhanced without departing from the scope of the claims described below. Other embodiments can be used in the subject disclosure.

It should be understood that devices described in the exemplary embodiments can be in communication with each other via various wireless and/or wired methodologies. The methodologies can be links that are described as coupled, connected and so forth, which can include unidirectional and/or bidirectional communication over wireless paths and/or wired paths that utilize one or more of various protocols or methodologies, where the coupling and/or connection can be direct (e.g., no intervening processing device) and/or indirect (e.g., an intermediary processing device such as a router).

Figure 9:
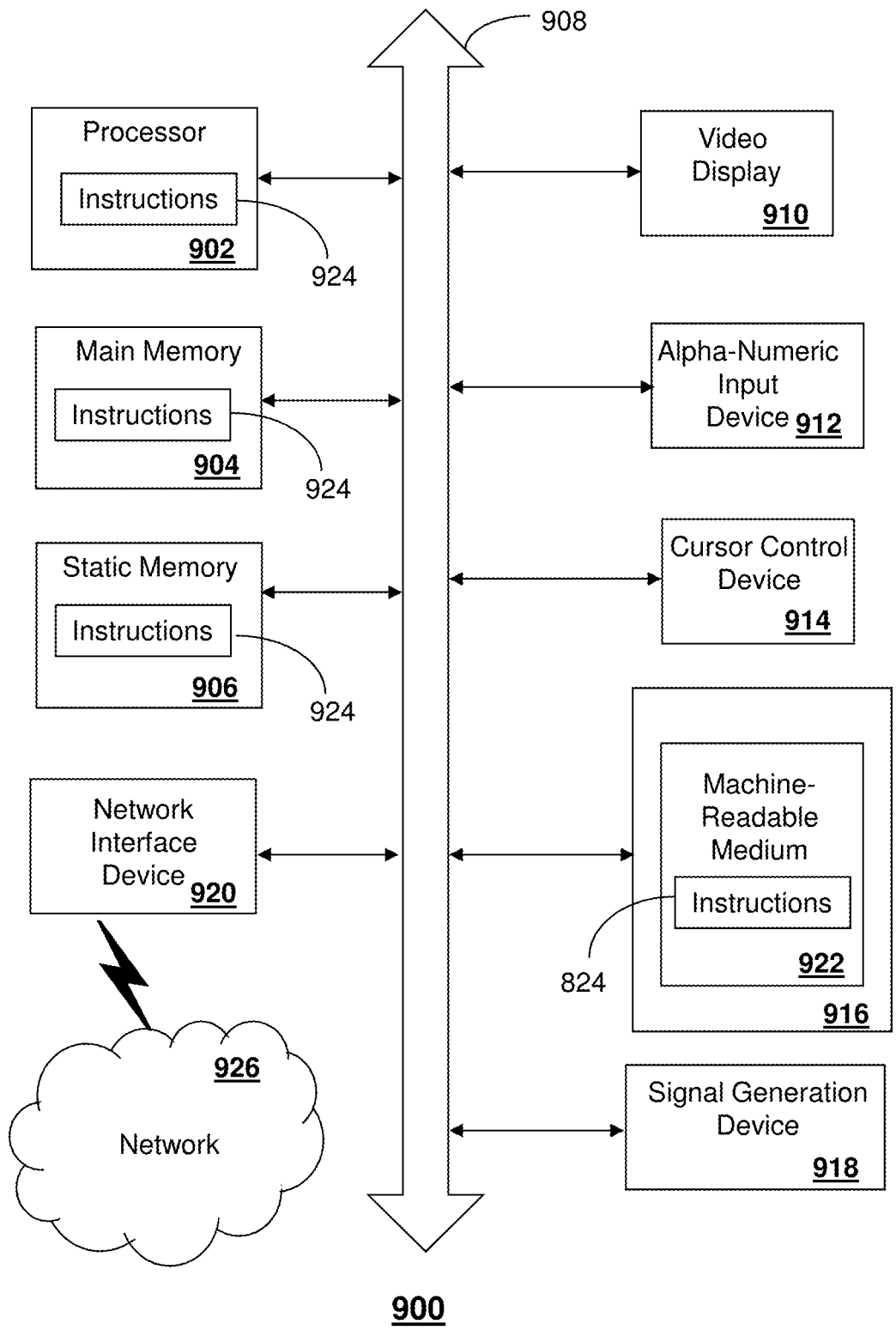
FIG. 9 is a diagrammatic representation of a machine in the form of a computer system within which a set of instructions, when executed, may cause the machine to perform any one or more of the methods described herein.

FIG. 9 depicts an exemplary diagrammatic representation of a machine in the form of a computer system 900 within which a set of instructions, when executed, may cause the machine to perform any one or more of the methods described above. One or more instances of the machine can operate, for example, as electronics unit 104, measurement unit 206, measurement device 502, remote device 504, server 506 measurement device 702, device 752 and/or other devices of FIGS. 1A, 1B, 2A, 2B, 3A, 3B, 5, 6A, 6B, 6C, 7A, 7B and/or 8. In some embodiments, the machine may be connected (e.g., using a network 926) to other machines. In a networked deployment, the machine may operate in the capacity of a server or a client user machine in a server-client user network environment, or as a peer machine in a peer-to-peer (or distributed) network environment.

The machine may comprise a server computer, a client user computer, a personal computer (PC), a tablet, a smart phone, a laptop computer, a desktop computer, a control system, a network router, switch or bridge, or any machine capable of executing a set of instructions (sequential or otherwise) that specify actions to be taken by that machine. It will be understood that a communication device of the subject disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methods discussed herein.

The computer system 900 may include a processor (or controller) 902 (e.g., a central processing unit (CPU)), a graphics processing unit (GPU, or both), a main memory 904 and a static memory 906, which communicate with each other via a bus 908. The computer system 900 may further include a display unit 910 (e.g., a liquid crystal display (LCD), a flat panel, or a solid state display). The computer system 900 may include an input device 912 (e.g., a keyboard), a cursor control device 914 (e.g., a mouse), a disk drive unit 916, a signal generation device 918 (e.g., a speaker or remote control) and a network interface device 920. In distributed environments, the embodiments described in the subject disclosure can be adapted to utilize multiple display units 910 controlled by two or more computer systems 900. In this configuration, presentations described by the subject disclosure may in part be shown in a first of the display units 910, while the remaining portion is presented in a second of the display units 910.

The disk drive unit 916 may include a tangible computer-readable storage medium 922 on which is stored one or more sets of instructions (e.g., software 924) embodying any one or more of the methods or functions described herein, including those methods illustrated above. The instructions 924 may also reside, completely or at least partially, within the main memory 904, the static memory 906, and/or within the processor 902 during execution thereof by the computer system 900. The main memory 904 and the processor 902 also may constitute tangible computer-readable storage media.

Dedicated hardware implementations including, but not limited to, application specific integrated circuits, programmable logic arrays and other hardware devices can likewise be constructed to implement the methods described herein. Application specific integrated circuits and programmable logic array can use downloadable instructions for executing state machines and/or circuit configurations to implement embodiments of the subject disclosure. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the subject disclosure, the operations or methods described herein are intended for operation as software programs or instructions running on or executed by a computer processor or other computing device, and which may include other forms of instructions manifested as a state machine implemented with logic components in an application specific integrated circuit or field programmable gate array. Furthermore, software implementations (e.g., software programs, instructions, etc.) including, but not limited to, distributed processing or component/object distributed processing, parallel processing, or virtual machine processing can also be constructed to implement the methods described herein. Distributed processing environments can include multiple processors in a single machine, single processors in multiple machines, and/or multiple processors in multiple machines. It is further noted that a computing device such as a processor, a controller, a state machine or other suitable device for executing instructions to perform operations or methods may perform such operations directly or indirectly by way of one or more intermediate devices directed by the computing device.

While the tangible computer-readable storage medium 922 is shown in an example embodiment to be a single medium, the term "tangible computer-readable storage medium" should be taken to include a single medium or multiple media (e.g., a centralized or distributed database, and/or associated caches and servers) that store the one or more sets of instructions. The term "tangible computer-readable storage medium" shall also be taken to include any non-transitory medium that is capable of storing or encoding a set of instructions for execution by the machine and that cause the machine to perform any one or more of the methods of the subject disclosure. The term "non-transitory" as in a non-transitory computer-readable storage includes without limitation memories, drives, devices and anything tangible but not a signal per se.

The term "tangible computer-readable storage medium" shall accordingly be taken to include, but not be limited to: solid-state memories such as a memory card or other package that houses one or more read-only (non-volatile) memories, random access memories, or other re-writable (volatile) memories, a magneto-optical or optical medium such as a disk or tape, or other tangible media which can be used to store information. Accordingly, the disclosure is considered to include any one or more of a tangible computer-readable storage medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are from time-to-time superseded by faster or more efficient equivalents having essentially the same functions. Wireless standards for device detection (e.g., RFID, NFC), short-range communications (e.g., Bluetooth®, WiFi, Zigbee®), and long-range communications (e.g., WiMAX, GSM, CDMA, LTE) can be used by computer system 900. In one or more embodiments, information regarding use of services can be generated including services being accessed, media consumption history, user preferences, and so forth. This information can be obtained by various methods including user input, detecting types of communications (e.g., video content vs. audio content), analysis of content streams, and so forth. The generating, obtaining and/or monitoring of this information can be responsive to an authorization provided by the user. In one or more embodiments, an analysis of data can be subject to authorization from user(s) associated with the data, such as an opt-in, an opt-out, acknowledgement requirements, notifications, selective authorization based on types of data, and so forth.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. The exemplary embodiments can include combinations of features and/or steps from multiple embodiments. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement which achieves the same or similar purpose may be substituted for the embodiments described or shown by the subject disclosure. The subject disclosure is intended to cover any and all adaptations or variations of various embodiments. Combinations of the above embodiments, and other embodiments not specifically described herein, can be used in the subject disclosure. For instance, one or more features from one or more embodiments can be combined with one or more features of one or more other embodiments. In one or more embodiments, features that are positively recited can also be negatively recited and excluded from the embodiment with or without replacement by another structural and/or functional feature. The steps or functions described with respect to the embodiments of the subject disclosure can be performed in any order. The steps or functions described with respect to the embodiments of the subject disclosure can be performed alone or in combination with other steps or functions of the subject disclosure, as well as from other embodiments or from other steps that have not been described in the subject disclosure. Further, more than or less than all of the features described with respect to an embodiment can also be utilized.

Less than all of the steps or functions described with respect to the exemplary processes or methods can also be performed in one or more of the exemplary embodiments. Further, the use of numerical terms to describe a device, component, step or function, such as first, second, third, and so forth, is not intended to describe an order or function unless expressly stated so. The use of the terms first, second, third and so forth, is generally to distinguish between devices, components, steps or functions unless expressly stated otherwise. Additionally, one or more devices or components described with respect to the exemplary embodiments can facilitate one or more functions, where the facilitating (e.g., facilitating access or facilitating establishing a connection) can include less than every step needed to perform the function or can include all of the steps needed to perform the function.

In one or more embodiments, a processor (which can include a controller or circuit) has been described that performs various functions. It should be understood that the processor can be multiple processors, which can include distributed processors or parallel processors in a single machine or multiple machines. The processor can be used in supporting a virtual processing environment. The virtual processing environment may support one or more virtual machines representing computers, servers, or other computing devices. In such virtual machines, components such as microprocessors and storage devices may be virtualized or logically represented. The processor can include a state machine, application specific integrated circuit, and/or programmable gate array including a Field PGA. In one or more embodiments, when a processor executes instructions to perform "operations", this can include the processor performing the operations directly and/or facilitating, directing, or cooperating with another device or component to perform the operations.

The Abstract of the Disclosure is provided with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A device comprising:
   a sleeve, wherein the sleeve has a first length that spans from a first end of the sleeve to a second end of the sleeve, wherein the sleeve has a first non-expanded circumference at a first location along the first length of the sleeve, wherein the sleeve has a second non-expanded circumference at a second location along the first length of the sleeve and wherein the sleeve has a third non-expanded circumference at a third location along the first length of the sleeve;
   a first elastic measurement element attached to the sleeve at the first location, the first elastic measurement element traversing a first portion of the first non-expanded circumference, the first elastic measurement element having a first end and a second end, and the first elastic measurement element being attached to the sleeve such that there is a first gap between the first end of the first elastic measurement element and the second end of the first elastic measurement element;
   a second elastic measurement element attached to the sleeve at the second location, the second elastic measurement element traversing a second portion of the second non-expanded circumference;
   a third elastic measurement element attached to the sleeve at the third location, the third elastic measurement element traversing a third portion of the third non-expanded circumference;
   a first conductor;
   a processing system including a processor; and
   a memory that stores executable instructions that, when executed by the processing system, facilitate performance of operations, the operations comprising:
      obtaining, from the first elastic measurement element, a first value representative of a first expanded circumference of the sleeve at a point in time when the sleeve is disposed on a limb of a person;
      obtaining, from the second elastic measurement element, a second value representative of a second expanded circumference of the sleeve at the point in time when the sleeve is disposed on the limb of the person, the second value being obtained via the first conductor that is routed through the first gap;
      obtaining, from the third elastic measurement element, a third value representative of a third expanded circumference of the sleeve at the point in time when the sleeve is disposed on the limb of the person;
      determining, based upon the first value, the second value, and the third value, a geometric profile along a second length of the limb; and
      outputting, to a computing device, data representing the geometric profile, the outputting of the data to the computing device enabling the computing device to present via a display a graphic visualization of a difference between the geometric profile and another geometric profile of the limb of the person that had been determined at another point in time that is different from the point in time at which the geometric profile had been determined.

2. The device of claim 1, wherein:
   the first elastic measurement element comprises a first elastic resistive element, wherein a first expansion of the first elastic resistive element provides a first change in resistance that correlates to the first expansion of the first elastic resistive element;
   the second elastic measurement element comprises a second elastic resistive element, wherein a second expansion of the second elastic resistive element provides a second change in resistance that correlates to the second expansion of the second elastic resistive element; and
   the third elastic measurement element comprises a third elastic resistive element, wherein a third expansion of the third elastic resistive element provides a third change in resistance that correlates to the third expansion of the third elastic resistive element.

3. The device of claim 1, further comprising:
   a second conductor;
   wherein the second elastic measurement element has a first end and a second end, and wherein the second elastic measurement element is attached to the sleeve such that there is a second gap between the first end of the second elastic measurement element and the second end of the second elastic measurement element;
   wherein the first conductor is routed through the first gap to direct a first signal from the second elastic measurement element to the processing system; and
   wherein the second conductor is routed through the second gap and the first gap to direct a second signal from the third elastic measurement element to the processing system.

4. The device of claim 1, further comprising:
a second conductor electrically connected with the second elastic measurement element and a third conductor electrically connected with the third elastic measurement element, the first conductor being electrically connected with the first elastic measurement element.

5. The device of claim 1, wherein:
the first elastic measurement element is disposed on the sleeve, the first elastic measurement element is disposed in the sleeve, or any combination thereof;
the second elastic measurement element is disposed on the sleeve, the second elastic measurement element is disposed in the sleeve, or any combination thereof; and
the third elastic measurement element is disposed on the sleeve, the third elastic measurement element is disposed in the sleeve, or any combination thereof.

6. The device of claim 1, wherein:
the first end of the sleeve is open and the second end of the sleeve is closed, such that the sleeve is in a form of a sock or a glove.

7. The device of claim 1, wherein the computing device comprises the display.

8. The device of claim 1, wherein the difference between the geometric profile and the another geometric profile is shown as a shaded area.

9. The device of claim 1, wherein:
the first end of the sleeve is open and the second end of the sleeve is open, such that the sleeve is in a form of a cuff or an arm band.

10. A machine-readable storage medium comprising executable instructions that, when executed by a system including a processor, facilitate performance of operations, the operations comprising:
obtaining a first plurality of circumference measurements, each of the first plurality of circumference measurements corresponding to a respective first circumference around a limb of a person at a respective one of a plurality of locations of the limb, each of the first plurality of circumference measurements being obtained from a respective one of a plurality of elastic measurement elements that is positioned at a respective one of the locations, each of the plurality of elastic measurement elements being attached to a sleeve that has a first length, a first one of the plurality of elastic measurement elements being disposed partially around the sleeve such that between a first end of the first one of the plurality of elastic measurement elements and a second end of the first one of the plurality of elastic measurement elements there is a first gap; a conductor being attached to a second one of the plurality of elastic measurement elements, and the conductor being routed from the second one of the plurality of elastic measurement elements through the first gap that is associated with the first one of the plurality of elastic measurement elements to direct a signal from the second one of the plurality of elastic measurement elements to the system;
determining, based upon the first plurality of circumference measurements, a first geometric profile along a second length of the limb;
obtaining a second plurality of circumference measurements, each of the second plurality of circumference measurements corresponding to a respective second circumference around the limb of the person at the respective one of the plurality of locations of the limb, the first plurality of circumference measurements being obtained at a first time, the second plurality of circumference measurements being obtained at a second time, and the second time being after the first time;
determining, based upon the second plurality of circumference measurements, a second geometric profile along the second length of the limb;
comparing the second geometric profile to the first geometric profile to generate difference data between the second geometric profile and the first geometric profile; and
presenting via a display a graphic visualization of the difference data, the graphic visualization showing a difference between the first geometric profile existing at the first time and the second geometric profile existing at the second time.

11. The machine-readable storage medium of claim 10, wherein:
each of the plurality of elastic measurement elements comprises an elastic resistive element such that for a given elastic resistive element an expansion thereof provides a change in resistance that correlates to the expansion.

12. The machine-readable storage medium of claim 10, wherein:
the first plurality of circumference measurements equals X number of measurements;
the plurality of locations equals X number of locations;
the plurality of elastic measurement elements equals X number of elastic measurement elements; and
X is an integer between 3 and 50, inclusive.

13. The machine-readable storage medium of claim 10, wherein the system comprises the display.

14. The machine-readable storage medium of claim 10, wherein the operations further comprise transmitting the data representing the first geometric profile to a remote device.

15. The machine-readable storage medium of claim 14, wherein the remote device comprises a database, and wherein the data representing the first geometric profile is stored in the database in association with an identity of the person.

16. The machine-readable storage medium of claim 10, wherein each of the plurality of elastic measurement elements is disposed on the sleeve, each of the plurality of elastic measurement elements is disposed in the sleeve, or any combination thereof.

17. The machine-readable storage medium of claim 10, wherein each of the plurality of elastic measurement elements comprises a resistance element having a first electrical resistance in an elongated state and a second electrical resistance in a non-elongated state, wherein the first electrical resistance is different from the second electrical resistance.

18. The machine-readable storage medium of claim 10, wherein:
the first end of the sleeve is open and the second end of the sleeve is closed, such that the sleeve is in a form of a sock or a glove; or
the first end of the sleeve is open and the second end of the sleeve is open, such that the sleeve is in a form of a cuff or an arm band.

19. A method comprising:
obtaining, by a system including a processor, a first value representative of a first expanded circumference of a sleeve at a point in time when the sleeve is disposed on a limb of a person, wherein the first value is obtained from a first elastic measurement element that is attached to the sleeve at a first location along a first length of the sleeve, the first elastic measurement element traversing a first portion of the first expanded circumference of the sleeve;

obtaining, by the system, a second value representative of a second expanded circumference of the sleeve at the point in time when the sleeve is disposed on the limb of the person, wherein the second value is obtained from a second elastic measurement element that is attached to the sleeve at a second location along the first length of the sleeve, the second elastic measurement element traversing a second portion of the second expanded circumference of the sleeve;

obtaining, by the system, a third value representative of a third expanded circumference of the sleeve at the point in time when the sleeve is disposed on the limb of the person, wherein the third value is obtained from a third elastic measurement element that is attached to the sleeve at a third location along the first length of the sleeve, the third elastic measurement element traversing a third portion of the third expanded circumference of the sleeve;

determining by the system, based upon the first value, the second value, and the third value, a geometric profile along a second length of the limb, the geometric profile being in a form that presents a first distance, a second distance and a third distance, the first distance being associated with the first location, the second distance being associated with the second location, the third distance being associated with the third location, the first distance being a first diameter of the limb at the first location, the second distance being a second diameter of the limb at the second location, and the third distance being a third diameter of the limb at the third location; and outputting by the system, to a display device, data to display a graphic visualization of a difference between the geometric profile and another geometric profile of the limb of the person that had been determined at another point in time that is different from the point in time at which the geometric profile had been determined.

20. The method of claim 19, wherein the first location along the first length of the sleeve corresponds to a first location along the second length of the limb, wherein the second location along the first length of the sleeve corresponds to a second location along the second length of the limb, and wherein the third location along the first length of the sleeve corresponds to a third location along the second length of the limb.

\* \* \* \* \*